(12) United States Patent
Hargrove

(10) Patent No.: US 8,846,407 B2
(45) Date of Patent: Sep. 30, 2014

(54) CHEMICAL EXPLOSIVE DETECTOR

(76) Inventor: James M. Hargrove, Riverside, CA (US)

( * ) Notice: Subject to any disclaimer, the term of this patent is extended or adjusted under 35 U.S.C. 154(b) by 302 days.

(21) Appl. No.: 13/524,971

(22) Filed: Jun. 15, 2012

(65) Prior Publication Data

US 2013/0017618 A1   Jan. 17, 2013

Related U.S. Application Data

(63) Continuation-in-part of application No. 12/703,582, filed on Feb. 10, 2010, now abandoned.

(60) Provisional application No. 61/151,320, filed on Feb. 10, 2009.

(51) Int. Cl.
*G01N 33/22* (2006.01)
*G01N 21/31* (2006.01)
*G01N 33/00* (2006.01)

(52) U.S. Cl.
CPC .......... *G01N 33/0024* (2013.01); *G01N 33/227* (2013.10); *G01N 21/31* (2013.01); *G01N 33/0013* (2013.01); *G01N 33/0057* (2013.01)
USPC ................. 436/156; 422/83; 422/91; 422/93; 436/107; 436/110; 436/116; 436/117; 436/118; 436/155; 436/157; 436/158; 436/164; 436/171

(58) Field of Classification Search
USPC ................... 422/52, 82.05, 82.09, 83, 91, 93; 436/107, 110, 116–118, 155–158, 164, 436/171
See application file for complete search history.

(56) References Cited

U.S. PATENT DOCUMENTS

| | | | |
|---|---|---|---|
| 3,430,482 A | 3/1969 | Dravnieks et al. | |
| 3,528,779 A | 9/1970 | Fontijn | |
| 3,647,387 A | 3/1972 | Benson et al. | |
| 3,652,227 A | 3/1972 | Harman, III et al. | |
| 3,877,875 A | 4/1975 | Jones et al. | |
| 3,934,991 A | 1/1976 | Frain et al. | |
| 5,092,218 A | 3/1992 | Fine et al. | |
| 5,854,077 A | 12/1998 | Wolfson et al. | |
| 5,906,946 A | 5/1999 | Sausa et al. | |
| 6,051,436 A | 4/2000 | Reagen et al. | |
| 6,346,419 B1 | 2/2002 | Ryerson et al. | |
| 6,419,634 B1 | 7/2002 | Gaston, IV et al. | |
| 6,503,758 B1 | 1/2003 | Allen et al. | |
| 6,635,415 B1 | 10/2003 | Bollinger et al. | |

(Continued)

OTHER PUBLICATIONS

Lee, Y.-W. et al, Industrial and Engineering Chemistry Research 2001, 40, 3337-3345.*

(Continued)

*Primary Examiner* — Arlen Soderquist
(74) *Attorney, Agent, or Firm* — Heidi Eisenhut, Esq.; Loza & Loza, LLP

(57) ABSTRACT

A method and device for detecting explosive compounds in an air sample in which the air sample is filtered with activated carbon treated with a weakly basic solution, after which the air sample is divided into two parts, with one part being heated at lower temperatures to decompose non-explosive nitrogenous compounds and the second part being heated at higher temperatures to decompose explosive nitrogenous compounds. Nitrogen dioxide is measured in both portions of the air sample with a spectrographic detector, and the presence or absence of explosive nitrogenous compounds in the air sample is determined.

19 Claims, 4 Drawing Sheets

(56) References Cited

U.S. PATENT DOCUMENTS

| | | |
|---|---|---|
| RE38,797 E | 9/2005 | Linker et al. |
| 7,029,920 B2 | 4/2006 | Lanier et al. |
| 7,301,639 B1 | 11/2007 | Kebabian et al. |
| 7,323,343 B2 | 1/2008 | Cox et al. |
| 2004/0053421 A1 | 3/2004 | Nguyen et al. |
| 2004/0262501 A1 | 12/2004 | Kajii |
| 2005/0045032 A1 | 3/2005 | Dasgupta et al. |
| 2006/0081073 A1 | 4/2006 | Vandrish et al. |
| 2006/0231420 A1 | 10/2006 | Garzon et al. |
| 2008/0134894 A1 | 6/2008 | Tsai et al. |
| 2008/0159341 A1 | 7/2008 | Patel et al. |
| 2008/0261322 A1 | 10/2008 | Burdinski |
| 2009/0027675 A1 | 1/2009 | Johnson et al. |
| 2009/0113982 A1 | 5/2009 | Hodyss et al. |
| 2009/0120212 A1 | 5/2009 | Hargrove et al. |
| 2009/0128819 A1 | 5/2009 | Van Kesteren et al. |

OTHER PUBLICATIONS

Brown, S. S., Chemical Reviews 2003, 103,5219-5238.
Day, D.A., et al., A thermal dissociation laser-induced fluorescence instrument for in situ detection of NO2, peroxy nitrates, alkyl nitrates and HNO3, J. of Geophysical Research-Atmospheres, 107:D5-6 (2002).
Hargrove, J. et al, Environmental Science and Technology 2006,40, 7868-7873.
Hargrove, J.M., The Application of Cavity Ring-Down Spectroscopy to Atmospheric and Physical Chemistry, University of California, Riverside, Riverside, Dec. 2007.
Kasyutich, V. L. et al, Measurement Science and Technology 2006, 17, 923-931.
Kebabain, P. L. et al, Analytical Chemistry 2005, 77, 724-728.
Kebabain, P. L. et al, Environmental Science and Technology 2008,42,6040-6045.
Mazely, T. L. et al, Journal of Physical Chemistry 1995, 99, 8162-8169.
Moore, D. S., Review of Scientific Instruments 2004,75,2499-2512.
Munson, C. A. et al, Report ARL-TR-4279, 2007, 76 pages.
Ramos, C. et al, Applied Optics 2007,46, 620-627.
Riris, H. et al, Applied Optics 1996, 35, 4694-4704.
Sadanaga, Y. et al, Review of Scientific Instruments 2004, 75, 864-872.
Smith J. M. et al, Journal of the Optical Society of America B 1995, 12, 964-969.
Spicer, J. B. et al, SPIE 2003, 5089, 1088-1094.
Steinfeld, J. I. et al, SPIE 1999, 3853, 28-33.
Todd, M. W. et al, Applied Physics B 2002,75,367-376.
Usachev, A. D. et al, Applied Spectroscopy 2001, 125-129.
Wong, D. M. et al, Spectrochimica Acta A 2007,67,1019-1024.

\* cited by examiner

US 8,846,407 B2

CHEMICAL EXPLOSIVE DETECTOR

CROSS-REFERENCE TO RELATED APPLICATIONS

The present application is a continuation-in-part of U.S. patent application Ser. No. 12/703,582, filed on Feb. 10, 2010 and entitled "HAZARDOUS CHEMICALS DETECTOR & METHODS OF USE THEREOF," which claims the benefit of priority from U.S. Patent Application No. 61/151,320 filed on Feb. 10, 2010. The disclosures of the foregoing applications are incorporated herein by reference in their entirety.

BACKGROUND

An explosive material is a material that contains a great amount of potential energy and which can produce an explosion if the energy is released suddenly, usually accompanied by the production of light, heat, sound, and/or pressure. Examples of explosive compounds include ammonium nitrate, nitroglycerin, acetone peroxide, trinitrotoluene (TNT), nitrocellulose, RDX, PETN, and HMX. Recently, the detection of explosives in venues such as ports, airports and other border entries has become important in view of the risk of terrorist attacks.

The detection of explosive compound residues has been attempted with a number of different technologies, including mass spectroscopy, fluorescence detection, and nitric oxide detection. Mass spectroscopy requires expensive and cumbersome equipment that needs frequent maintenance. Fluorescence detection may not be sensitive enough for all applications, and requires that samples be accessible to sampling by wipes that are then irradiated to detect any residue. Nitrogen monoxide detection has been developed based on the principle that many explosives can be made to generate nitrogen monoxides. Conventional equipment used in these techniques is relatively insensitive, requires frequent calibration and service, and may not detect explosives.

SUMMARY

The present invention comprises a method and device for detecting explosive compounds. In the present method, an air sample is collected in the vicinity of an object, and the air sample is then conducted through a filter comprising a porous material, such as granular activated carbon, treated with a solution having a basic pH, in order to remove ambient NO and $NO_2$ from the air sample. The activated carbon is preferably treated with a solution having a pH of between 9 and 12, more preferably a pH of about 10, and in preferred embodiments the basic solution with which the activated carbon is treated comprises calcium hydroxide or magnesium hydroxide. The air sample is then preferably passed through a filter having a pore size of between 3 and 20 microns.

In this process, the air sample is then divided, with a first portion being conducted through a heater comprising a chamber heated to a temperature of between 80° C. and 200° C., preferably to 120° C., in order to convert non-explosive nitrogenous compounds to NO or $NO_2$, and a second portion of being conducted through a heater comprising a chamber heated to a temperature of between 250° C. and 350° C., preferably to 290° C., in order to convert non-explosive and explosive nitrogenous compounds to NO or $NO_2$. In each case the air stream is preferably exposed to the heated environment within the heater for between 0.05 and 0.5 seconds. Each of the air sample portions is then spectrographically evaluated in order to measure the amount of $NO_2$ in both portions of the air sample. By comparing whether the amount of $NO_2$ in the second portion of the air sample is greater than the amount of $NO_2$ in the first portion of the air sample, the presence of an explosive compound in the air sample can be determined.

In an alternative process, explosive compounds can be detected by collecting an air sample in a vicinity of an object and conducting the air sample through a filter comprising granular activated carbon treated with a solution having a pH of between 9 and 12, preferably treated with calcium hydroxide or magnesium hydroxide having a pH of 10, to remove ambient $NO_2$. The air sample is then conducted through a heater comprising a chamber heated to a temperature of between 250° C. and 350° C., preferably for between 0.05 and 0.5 seconds, in order to convert non-explosive and explosive nitrogenous compounds to $NO_2$. The resulting $NO_2$ in the air sample is then spectrographically measured in order to determine the amount of $NO_2$ in the air sample, thereby determining whether an explosive compound is present in the air sample.

A device for use in the foregoing method preferably includes:
  (a) an inlet for receiving an air sample;
  (b) a filter downstream of the inlet, the filter comprising a porous material such as granular activated carbon or a similar substrate treated with a solution having a basic pH;
  (c) a first conduit for receiving a first portion of the air sample, the first conduit being in communication with:
    (i) a first heater adapted to heat the sample to a temperature of between 80° C. and 200° C.; and
    (ii) a first spectrometer for measuring a quantity of $NO_2$ in the first portion of the air sample;
  (d) a second conduit for receiving a second portion of the air sample, the second conduit being in communication with:
    (i) a second heater adapted to heat the sample to a temperature of between 250° C. and 350° C.; and
    (ii) a second spectrometer for measuring a quantity of $NO_2$ in the first portion of the air sample; and
  (e) one or more pumps in communication with the air sample for drawing the air sample into the inlet of the device and expelling the measured air sample out of an outlet of the device.

The inlet preferably further includes a sampling tube within the inlet that directs the first portion of the air sample and the second portion of the air sample to the filter comprising activated carbon. The spectrometers used in this device can be, for example, cavity attenuated ring down spectrometer with gated integrated detection (CARDS-GID), a cavity phase shift spectroscopy (CAPS)-based instrument, cavity enhanced absorption (LEAS), or a laser-induced fluorescence detector (LIE). In an alternative embodiment, the present device can further include a source of nitrogen monoxide in communication with the second heater, for use in detecting non-nitrogenous explosive compounds that will oxidize NO to $NO_2$.

FIGURES

DESCRIPTION

The present apparatus and method allow the detection of trace quantities of explosive components, in particular nitrates and nitro compounds. Explosive compounds are detected by taking an air sample and then processing the air sample to enable accurate detection of an explosive compound in the air sample, if present. With respect to the detection of many common nitrogen-containing explosive compounds, processing the air sample comprises heating the sample to produce nitrogen dioxide ($NO_2$). With respect to nitrogen-containing compounds that preferentially generate nitrogen monoxide (NO) rather than nitrogen dioxide ($NO_2$) when heated, gas titration can be integrated into the system to convert nitrogen monoxide (NO) to nitrogen dioxide ($NO_2$). The resultant nitrogen dioxide can be detected by a spectrometer such as a cavity-attenuated ring down spectrometer with gated integrated detection (CARDS-GID), a cavity phase shift spectroscopy (CAPS)-based instrument, or a laser-induced fluorescence detector (LIF).

The present system has several advantages over conventional systems used to detect explosive materials. Unlike systems which make use of mass spectroscopy, the detectors used in the present system, such as a CRDS analyzer, are less complicated, relatively inexpensive, and do not need calibration or maintenance as frequently. The present system also removes ambient $NO_2$ more effectively than current analyzers and provides a more accurate measurement of generated $NO_2$ concentrations by removing background noise.

DEFINITIONS

As used herein, the following terms and variations thereof have the meanings given below, unless a different meaning is clearly intended by the context in which such term is used.

"Activated carbon" refers to a form of carbon that has been processed to make it extremely porous and thus to have a very large surface area available for adsorption or chemical reactions. The activated carbon used in the present system is typically a granular activated carbon, i.e. a material composed of granules generally having a minimum size of about 0.3 mm such that 95% of such granules are retained by a U.S. Standard Mesh Size No. 50 sieve (0.297 mm).

"Heater" refers to the component of the present system used to heat an air stream.

"Spectrometer" refers to an instrument that measures properties of light in order to analyze materials. Examples of spectrometers include cavity phase shift spectroscopy and cavity ring-down spectroscopy.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Explosive Detector System

Figure 1:
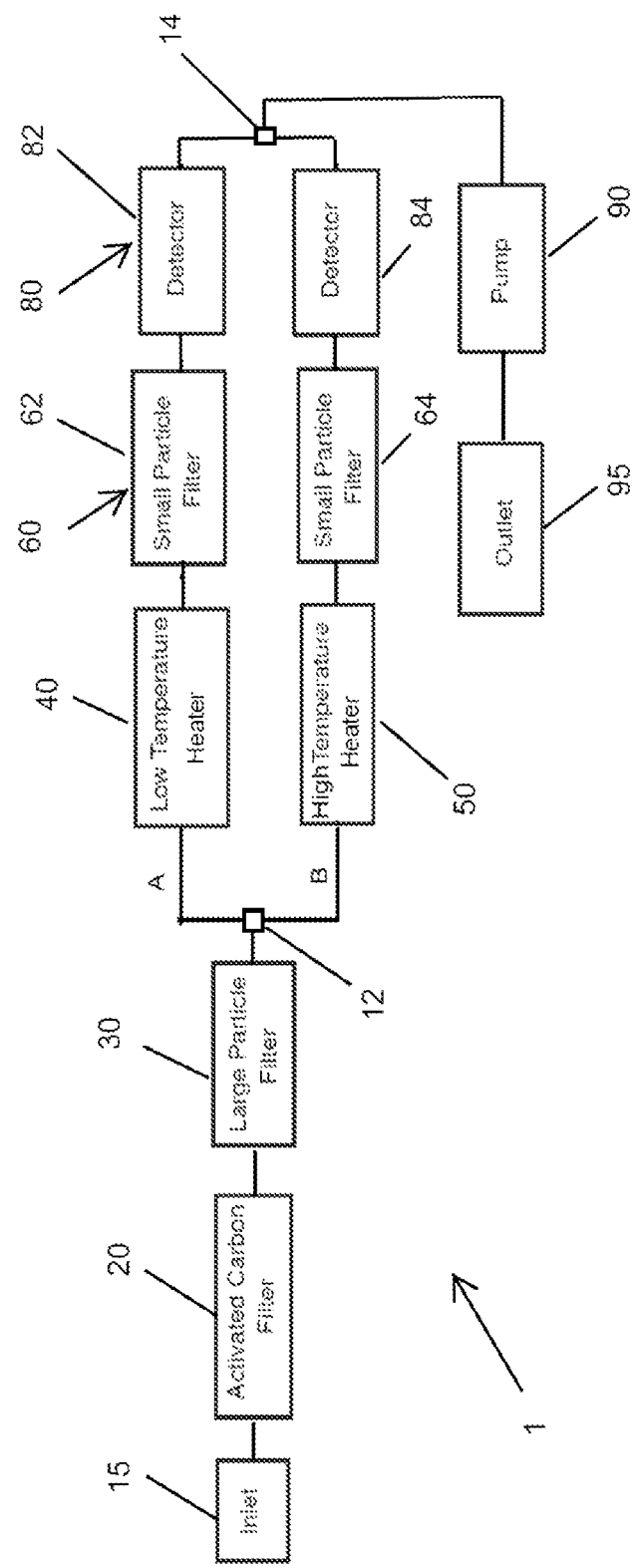
FIG. 1 is diagram of the components of an embodiment of the present explosive detector.

FIG. 1 illustrates an embodiment of the present device 1 for detecting and measuring nitrogenous explosive compounds in an air sample. The air sample to be tested is drawn through an opening of an inlet 15 by a pump 90 located downstream of the inlet 15. The inlet 15 comprises a conduit having an outer perimeter in contact with the atmosphere of an area to be tested. The conduit typically comprises a ⅜ inch diameter inert tube which collects an air sample at a rate of between approximately 2 and 10 liters/minute from the vicinity of an item or area to be tested. The air sample is typically at room temperature, and in any event is at least below the temperatures to which the heaters (40, 50) of the present device 1 are heated.

In a preferred embodiment, a smaller diameter tube, typically ⅛ in outer diameter is located within the larger diameter tube. The smaller diameter tube preferably collects a portion of the air sample from the larger tube at a rate of between 0.05 and 1 liter per minute, and more preferably at a rate of about 0.2 liters per minute. The opening of the smaller diameter tube is preferably located downstream of the outer perimeter of the inlet 15 and faces in a direction opposite to or tangentially with respect to the flow of air through the larger diameter tube, in order to collect a mixed or homogenized portion of the air sample for further testing. The remaining air flow, i.e. the portion of the air sample not directed into the device 1 for further testing, can be directed to the heaters (40, 50) of the device 1, preferably after being passed through a large particle filter (described below), in order to regulate the temperature of such heaters and cool them when necessary.

The air sample to be tested is then conducted through a treated activated carbon filter 20 in order to remove ambient nitrogen dioxide from the air sample. At a flow rate of between 1 and 3 liters per minute, a treated activated carbon filter as described below preferably comprises between 1 and 20 grams of the activated carbon material, and in any event less than 100 grams of material in order to avoid having explosive compounds being absorbed by the filter (and result in a false negative test result). Following this, the air sample is preferably conducted through a large particle filter 30 (also described below).

Following such filtration, the air sample is then divided into two streams at a junction 12. One stream, designated "A" in FIG. 1, is diverted through one or more conduits to a low temperature heater for treatment at between approximately 80° C. and 200° C., and preferably at a temperature of over 100° C., such as a temperature of 120° C. or 150° C. The air stream (which may not heat to the temperature of the heater) is within a chamber of the heater at the predetermined temperature for between 0.05 and 0.5 seconds in order to heat the nitrates and nitro compounds in the air stream (which heat faster than other components because they absorb infrared energy). Heating the air sample at such temperatures will convert alkyl peroxy-nitrates (PANs) and most other non-explosive nitrogenous compounds not trapped by the activated carbon filter into $NO_2$, but won't decompose most explosive nitrate compounds. The heated air sample can then optionally be passed through a small particle filter 62 before being directed to a spectrometer 82, which measures a spectrographic signal generated by the sample.

The second portion of the air stream, designated "B," is passed via a second conduit or set of conduits to a high temperature heater 50. This portion of the air sample is heated to between approximately 250° C. and 350° C., preferably to between about 290° C. and 300° C. The air stream (which may not reach the temperature of the heater) is conducted through a chamber in the heater that is heated to the predetermined temperature for between 0.05 and 0.5 seconds in order to heat the nitrates in the air stream (which heat faster than other components because they absorb infrared energy). Heating the air stream at such temperatures decomposes explosive nitrates and nitro compounds, such as ammonium nitrate and trinitrotoluene (TNT), as well as non-explosive nitrates, and converts them to $NO_2$. This portion of the air sample can then optionally be passed through a small particle filter 64 before being directed to a spectrometer 84, which measures a spectrographic signal generated by the "B" portion of the air sample.

Figure 3:
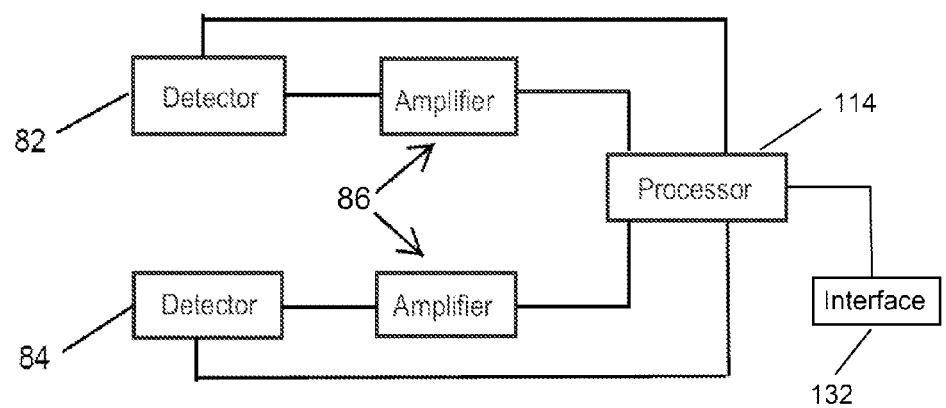
FIG. 3 is a diagram of a dual channel amplifier circuit for use in the present system.

As shown in FIG. 3, both of the spectrometers 82 and 84 are in electrical communication with a processor, which can be part of a general-purpose computer or of dedicated circuitry. The processor receives the spectrographic signals measured by each of the spectrometers 82 and 84 and analyzes them to determine whether an explosive nitrate is present in the air sample. The results of such analysis are then displayed, either on a general purpose computer or on an interface 132 included in the present device 1, which can be for example a light bar displaying results using a log scale.

The portion of the air stream that is subjected to lower temperature heating is generally used as a control, since the $NO_2$ measured in this sample includes the reaction products of non-explosive compounds as well as any ambient $NO_2$ not captured by the activated carbon filter. The amount of $NO_2$ detected in this control sample can be subtracted from the amount of $NO_2$ measured in the "B" portion of the air sample subjected to higher temperatures, which will include $NO_2$ generated from explosive nitrogenous compounds, in order to more accurately determine the presence of such explosive compounds. The presence of a greater quantity of $NO_2$ in the high-temperature treated portion of the air sample as compared to the low-temperature treated portion of the air sample can indicate the presence of an explosive nitrate in the air sample. The present system is able to detect nitrogenous explosive compounds at a sensitivity of between 0.01 and 1.0 parts per billion, although a threshold limit of 5 to 10 parts per billion is preferred in order to avoid false positive readings by the present device 1. Preferably, the rate of absorption of light by $NO_2$ is measured rather than the intensity of an $NO_2$ signal, as intensity measurements tend to vary more due to variation in light output by lasers.

Flow meters can be located before the junction 12, in order to measure the total air flow into the device 1, and/or downstream of the junction 12, in order to measure the flow and volume of the "A" and "B" air stream portions separately. Ball flow meters can be used to measure flow, for example, though mass flow meters are preferred for quality control due to their greater accuracy and computer output.

The "A" and "B" portions of the air sample are preferably drawn through the foregoing components of the present device 1 by suction through the use of a pump 90, which then expels the treated air sample through an outlet 90. In the embodiment illustrated in FIGS. 1 and 3, the "A" and "B" portions of the air sample are reunited into a single stream at a junction 14 prior to being drawn into the pump 90, although this is not required. The use of more than one pump, including pumps located upstream of the pump 90, can be used in alternative embodiments of the present device 1.

The present system can be incorporated into a housing adapted to be transported to a location in need of explosive screening. The system can incorporate components, preferably including a battery or other power supply, and are preferably less than 20 pounds in weight in order to be transportable by an individual, in which case the housing can be outfitted with a handle for holding and carrying the system. The system can also be incorporated into another device or system, such as a robot adapted to approach a location suspected of harboring an explosive compound.

System Components

Filters

After an air sample is collected for measurement with the present device, the sample is preferably filtered to remove, for example, large particles, ambient nitrogen dioxide ($NO_2$), and/or water vapor before the sample is heated. Larger particles can interfere with signal detection by obscuring signals caused by smaller particles, and are therefore preferably removed, such as with a particle filter. Filters having a pore size of between 2 and 20 microns or higher can be used as large particle filters, with pore sizes of between 3 and 5 microns being preferred, as ammonium nitrate particles generated near sources are typically about 2.5 microns or smaller. Alternatively, large particles can be removed with a cyclone, which creates a vortex in which heavier particles (such as mineral dust, dirt, or pollen) strike the walls of the cyclone and fall into a collecting cup or chamber.

A separate filter or filters can also be placed in-line with the flow of the air sample to remove water and other contaminants or analytes not of interest. To remove water vapor, for example, a water permeable membrane that does not absorb nitrates such as a PERMAPURE™ tube (available from Perma Pure LLC, Toms River, N.J.). To remove hydrocarbons, carbon filters such as those containing activated carbon can be used, for example.

Ambient $NO_2$ is preferably removed from an incoming airflow before it reaches the heaters or analyzers of the present device 1. While untreated activated carbon can remove up to 50% of atmospheric $NO_2$ entering the present device, virtually all of the ambient $NO_2$ can be removed (reduced to a level of less than 100 parts per trillion) by increasing the pH of the activated carbon filter, such as by treating the activated carbon with a basic solution or compound. Most explosive compounds are not acidic and not highly organic, and so tend to pass through an activated carbon filter having a basic pH while acidic and more organic compounds are captured by the filter.

The activated carbon for use in the activated carbon filter is preferably treated with a relatively weakly basic solution having a pH of between about 9 and 12, such as a solution comprising calcium hydroxide, magnesium hydroxide, potassium hydroxide, and/or sodium hydroxide. Preferably a solution comprising calcium hydroxide having a pH of approximately 10 is used. Optionally, activated carbon can also be treated with a weak acid. In a preferred embodiment, the activated carbon of the activated carbon filter is treated with a water-sequestering compound such as glycerin, propane diol, a polyglycol, or ethylene glycol. Such compounds help to remove water out from the air sample, keep basic compounds in the solution such as CaOH "activated," and also hold water to act as a reactant for impurities in the air sample. In addition, such compounds include —OH groups for reacting with impurities. In order to provide basic moieties in the activated carbon material, a relatively less caustic base such as calcium hydroxide is preferably used, in order to mitigate irritation or injury that could be caused by more caustic bases if a user were exposed to the activated carbon composition. Other porous materials, such as porous ceramic materials, can be used in place of activated carbon.

A preferred basic activated carbon filter for use in the present device is sold under the trade name ACTINITE B, and is available from ALTI LLC (Costa Mesa, Calif.). Such activated carbon can be prepared by mixing a slurry of $Ca(OH)_2$ with water and glycerine, pouring the mixture over granular activated charcoal, and then drying the mixture in an oven. Such activated carbon should be replaced at regular intervals, as exposure to air and/or nitrates for an extended period will eventually cause the activated carbon filter to begin absorbing explosive nitrate compounds.

Following the heat treatment of the air sample, the sample stream can optionally be filtered with a smaller pore filter 60, preferably a filter with a pore size of 1.0 microns or less, such as a 0.45 micron filter. Such small pore size filters remove particles that would cause scattering in the spectrometer, and such scattering is a source of both noise and interference in such detectors. The filter can, for example, be a Teflon filter.

Heaters

Any of a number of conventional heaters can be used in the present device in order to generate nitrogen dioxide (or nitrogen monoxide) from nitrogen-containing compounds in the sample, including convection heaters comprising a heater wire. The portions of the heater which contact air samples in the present device should be made from materials which are nonreactive with nitrogen dioxide. Materials such as nickel thus should not be used. The sample-contacting portions of the heaters are also preferably made from a material which does not absorb $NO_2$ at the elevated temperatures at which the heaters operate. Preferred materials include anodized aluminum and siliconized coated steel such as SILICOSTEEL (steel coated with a protective barrier of amorphous silicon material inter-diffused with the host substrate as described in U.S. Pat. No. 6,511,760, available from Restek Corporation, State College, Pa.). Other materials that can be used include quartz and non-porous ceramic materials.

Detectors

Figure 2:
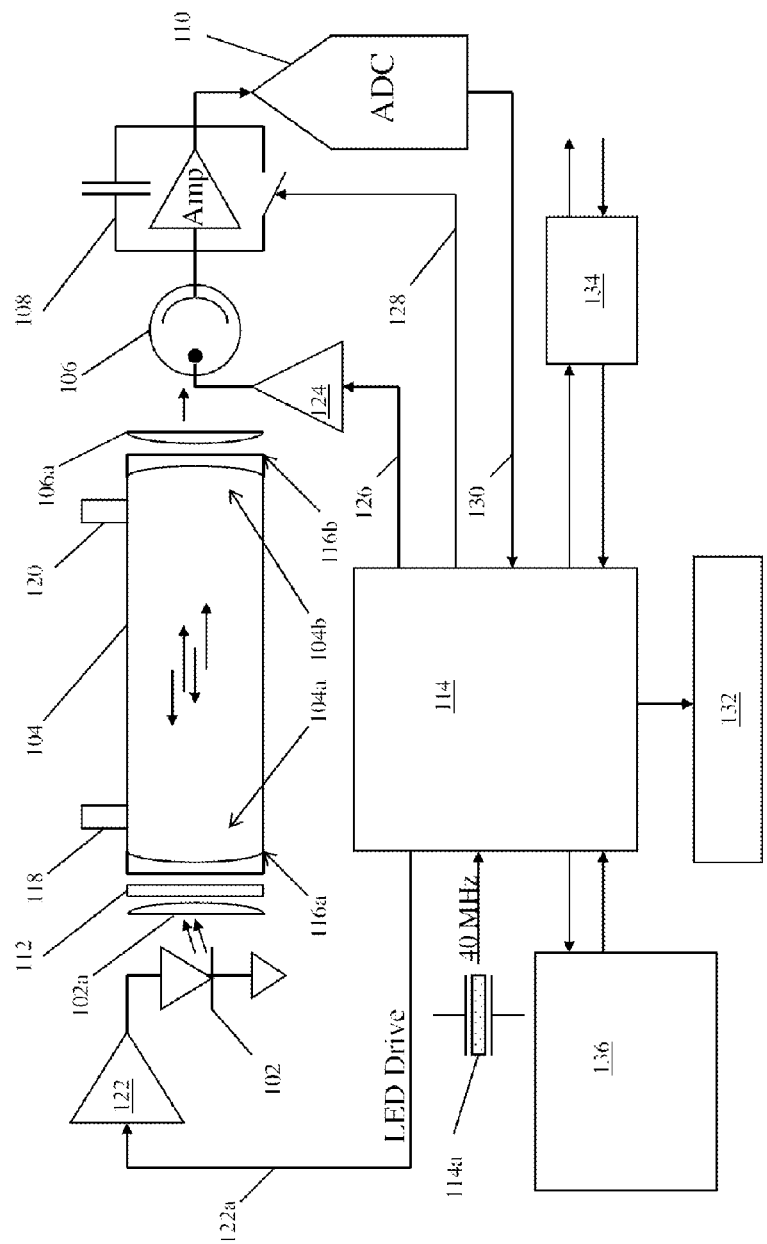
FIG. 2 is a diagram of a cavity ring-down spectroscopy (CRDS) analyzer that can be used in the present explosive detector.

Nitrogen dioxide is preferably detected and quantified by the present device using a spectrometer. In a preferred embodiment, the spectrometer used in the present device comprises a cavity ring-down spectroscopy (CRDS) apparatus 100, as described in U.S. Pat. No. 8,098,377. An exemplary arrangement showing a single spectrometer 80 is shown in FIG. 2. Principle components of CRDS 100 generally include (upstream to downstream) a light source 102, an optical cavity 104, a detector 106, an integrator 108 and a converter 110. Light source 102, with the aid of an associated lens or lenses 102a, is directed toward a proximal end 104a of optical cavity 104 while a distal end 104b of optical cavity 104 is directed toward detector 106 with the aid of an associated lens 106a. A bandpass filter 112 is positioned between light source 102 and proximal end 104a of optical cavity 104. In an alternative embodiment, bandpass filter 112 is positioned between distal end 104b of optical cavity 104 and detector 106. The bandpass filter 112 is adjusted to detect nitrogen dioxide.

Detector 106 is in electrical communication with integrator 108, and integrator 108 is in electrical communication with converter 110. All components (i.e., light source 102, optical cavity 104, detector 106, integrator 108 and converter 110) are controlled and/or driven by a processor 114, which can be part of a general-purpose computer or can be dedicated to the spectrometer. A quartz crystal oscillator 114a provides a stable and accurate timing source for computer 114 instruction stepping and timing and, in turn, for the integration measurement interval.

In one embodiment, light source 102 is a non-coherent light source such as a light-emitting diode (LED). Other examples of light sources include, but are not limited to, a laser, a blackbody radiator, a flashlamp discharge or other gas discharge. In embodiments in which light source 102 is an LED, the LED color and bandpass filter color are selected to provide light in a preferred narrow spectral bandwidth, in this case for the detection of nitrogen dioxide.

The optical cavity 104 can include two highly reflective plano/concave minors 116a and 116b situated internally at each end therein (i.e., at proximal end 104a and distal end 104b of optical cavity 104). Each mirror 116a, 116b can have a diameter of approximately one half inch (1.2 centimeters). In some embodiments, optical cavity 104 can have a cylindrical shape and is, for example, between about 0.25 inches (0.635 centimeters) to about 1.50 inches (3.81 centimeters) in diameter, preferably about one half inch (1.2 centimeters) in diameter, i.e., approximately close to the effective diameter of each mirror 116a, 116b. The distance between minors 116a and 116b is, for example, between about three (3) inches (6 centimeters) and about fifty (50) inches (127 centimeters). The present device preferably uses relatively low reflectivity mirrors (i.e., having a reflectivity of 99.9-99.99) because such minors provide more light output.

A sample inlet 118 is in fluid communication with (or coupled to) optical cavity 104, and, similarly, a pump inlet 120 is also in fluid communication with (or coupled to) optical cavity 104. During operation of CRDS 100, a sample is introduced into optical cavity 104 via sample inlet 118 and removed from optical cavity 104 via pump inlet 120.

The detector 106 with the aid of lens 106a (i.e., proximate to distal end 104b of optical cavity 104) functions to collect photons emitting from optical cavity 104 continuously or during predetermined time intervals (explained in more detail below). Detector 104 can be, for example, a phototube (PT), a photomultiplier tube (PMT), or an avalanche photodiode (APD). Integrator 108 (in electrical communication with detector 106) collects a current sample from detector 106 while converter 110 (in electrical communication with integrator 108) measures output voltage from integrator 108.

A processor 114 preferably drives light source 102 (arrow 122a), e.g., LED 102, via an amplified buffer 122 by generating a square wave input current which results in LED 102 being repeatedly turned ON and OFF. The amplified buffer 122 can use a constant current source to stabilize the output light level of the LED 102. The period of the resultant modulated current is preferably chosen to be approximately (4*τ) where τ is a time in microseconds. For example, if τ is two (2) microseconds, then the LED drive period would be eight (8) microseconds and the frequency would be nominally one-hundred and twenty-five (125) kilohertz (KHz). In another example, if τ is twenty (20) microseconds, then the LED drive period would be eighty (80) microseconds and the frequency would be nominally twelve and one-half (12.5) KHz. Pulsed light emanating from LED 102 then illuminates optical cavity 104. The light level in optical cavity 104 builds up, i.e., rises, while LED 102 is ON and then decays, i.e., falls, while LED 102 is OFF.

The light escaping from distal end 104b of optical cavity 104 is focused on to detector 106 with the aid of lens 106a which in turn converts the photons from the light into electrons. Detector 106 collects the photons emitted from optical cavity 104 only when gated (i.e., driven ON by an amplified buffer 124). There are two separate measurements made, one during the "ring up" or rise time portion of the resonant cavity cycle (LED 102 ON) and the other during the "ring down" or fall time portion of the resonant cavity cycle (LED 102 OFF). The sample time signal output (arrow 126) from computer 114 to detector 106 defines this gated detection time (see FIGS. 2-3). This process gives a small current sample which is collected in integrator 108. This process is repeated over, for example, ten-thousand to one hundred thousand sample readings (i.e., for about 0.1 to 1 second) which in turn creates a significant output voltage at integrator 108 (see FIGS. 4-5). The output voltage is then measured by converter 110, which is, for example, a high-resolution analog-to-digital converter. After the end of the previous measurement cycle and before the beginning of the next measurement cycle, the integrator 108 is reset (arrow 128) by processor 114 and the initial output voltage of integrator 108 is measured by converter 110, i.e., the initial output voltage of integrator 108 is measured between cycles. Measuring the initial output voltage of the integrator is more accurate than assuming the reset output voltage is "zero". The difference between the final output voltage and the initial output voltage is the measure of charge (photons) collected during the sampling of the "rise" time over the measurement interval. This process is repeated for the "fall time" or "ring down" portion of the resonant cavity cycle, i.e., when LED 102 is OFF. The "rise" time signal or ring-up (i.e., photons captured when LED 102 is ON) and the "fall" time signal or ring-down (i.e., photons captured when LED 102 is OFF) are consequently measured and is used to calculate a ratio, more particularly, the ratio of the difference between the rise time and the fall time (i.e., rise time minus fall time) divided by the sum of the rise time and the fall time (i.e., rise time plus fall time), represented by the following formula:

$$\text{Ratio} = \frac{\text{rise time} - \text{fall time}}{\text{rise time} + \text{fall time}}$$

This ratio is used to calculate the decay rate (k) represented by the foregoing. This ratio can also be the sum of many measurements.

After measurement of the output voltage of the integrator 110, processor 114 receives the given measurement (arrow 130) and generates a reading. Such reading is used to calculate the decay time constant ($\tau 0$) of an empty optical cavity 104 and changes in the decay time ($\tau$) caused by addition of an absorbing gas or scattering particles to the gas sample. The decay time constant ($\tau 0$) of an empty optical cavity 104 and changes in the decay time ($\tau$) are then used as a reference to calculate concentration of an absorbing gas (explained in more detail below). The concentration of the absorbing gas is displayed on user interface 132 or sent to an external computer before or after processing using the external data link (arrow 134). Processor 114 also serves as the regulator and/or controller for the various functions while the CRDS 100 is in operation. For example, processor 114, which in some embodiments is a single microchip, controls the square-wave drive of the light source 102 (arrow 102*a*), the sampling width, position and the interval of the measurement time (arrow 126) of detector 106, and resetting (arrow 128) of the integrator 108. Processor 114 can also serve to measure and control the environment (box 136), i.e., processor 114 can measure the atmospheric pressure and temperatures within the unit, and/or, stabilize the temperature of optical cavity 104 and electronics (i.e., making the quartz crystal oscillator 114*a* more stable) by controlling heaters to keep the temperature constant. Processor 114 can also serve to calculate the mathematical algorithms necessary to correlate the readings with the quantity of gas detected and/or measured.

The present device preferably comprises two spectrometers 80 and is a dual channel analyzer, as shown in FIG. 3, in which the processing circuitry 114 of the analyzer receives signals from each of the spectrometers (82, 84) of the present system simultaneously via an amplifier 86 dedicated to each spectrometer. This reduces the temperature sensitivity of the system by having the two lasers or LEDs of the spectrometers 80 responding to any changes in temperature in tandem. A dual channel configuration also eliminates interferences better, since a source of interference which affects both spectrometers, such as the presence of a solvent or other contaminant, will generally affect both spectrometers equally and the resulting signal interference will be canceled out when the background signal generated by the low temperature heater is compared with the signal generated by the air stream subjected to the high temperature heater.

One type of CRDS apparatus which can be used in the present system is a Cavity Attenuated Ring Down Spectroscopy-Gated Integrated Detection (CARDS-GID) apparatus, as described for example in US Patent Publication No. 2009-0120212 (see also Hargrove, J. M., The Application of Cavity Ring-Down Spectroscopy to Atmospheric and Physical Chemistry, University of California, Riverside, Riverside). In a CARDS-GID system, the decay of the light source is measured by analog integration. In an alternative embodiment, the phase shift of the light can be measured, i.e. the spectrometer can operate based on cavity phase shift spectroscopy (CAPS). The spectrometer can alternatively be a laser-induced fluorescence detector (LIF) or another type of spectrometer.

Process

In the present method for detecting explosive compounds, an air sample is first collected, heated, and then subjected to a detection method. A test area is sampled by drawing air from the vicinity of the test area through the inlet of the device. The test area can be, for example, the vicinity of a person, a piece of luggage, or a cargo box. Preferably the sample is collected within half a meter of the person, area, or item being tested.

The most straightforward manner of collecting an air sample is through the direct collection of air through a nozzle or other structure at an inlet of the present device. However, an air sample can alternatively be collected in a clean container and mechanically transported to the present device for testing, in which case the air sampling can be effectuated through the use of an enclosure that is flushed with air to draw out and mix the sample. To detect explosive compositions that generate nitrogen dioxide ($NO_2$) when heated, the air sample can be introduced into a heater as described above to generate $NO_2$ from any nitrogen-containing explosive compounds (if present). Finally, the sample can be introduced into a nitrogen dioxide detector such as a CRDS cavity to detect the amount of nitrogen dioxide, if any, which is indicative of the presence of nitrogen-containing explosive compounds in the air sample.

Non-Nitrogenous Explosive Compounds

The present system can also be adapted to detect some non-nitrogen-containing explosive compounds, in particular oxygen-containing explosive compounds. When such compounds are heated, they generate compounds that include oxygen radicals and ozone. If such compounds are then exposed to a source of nitrogen monoxide (NO), the reaction of the NO with such oxygen radicals or ozone can generate nitrogen dioxide ($NO_2$), which can then be detected as in other embodiments of the present system.

Figure 4:
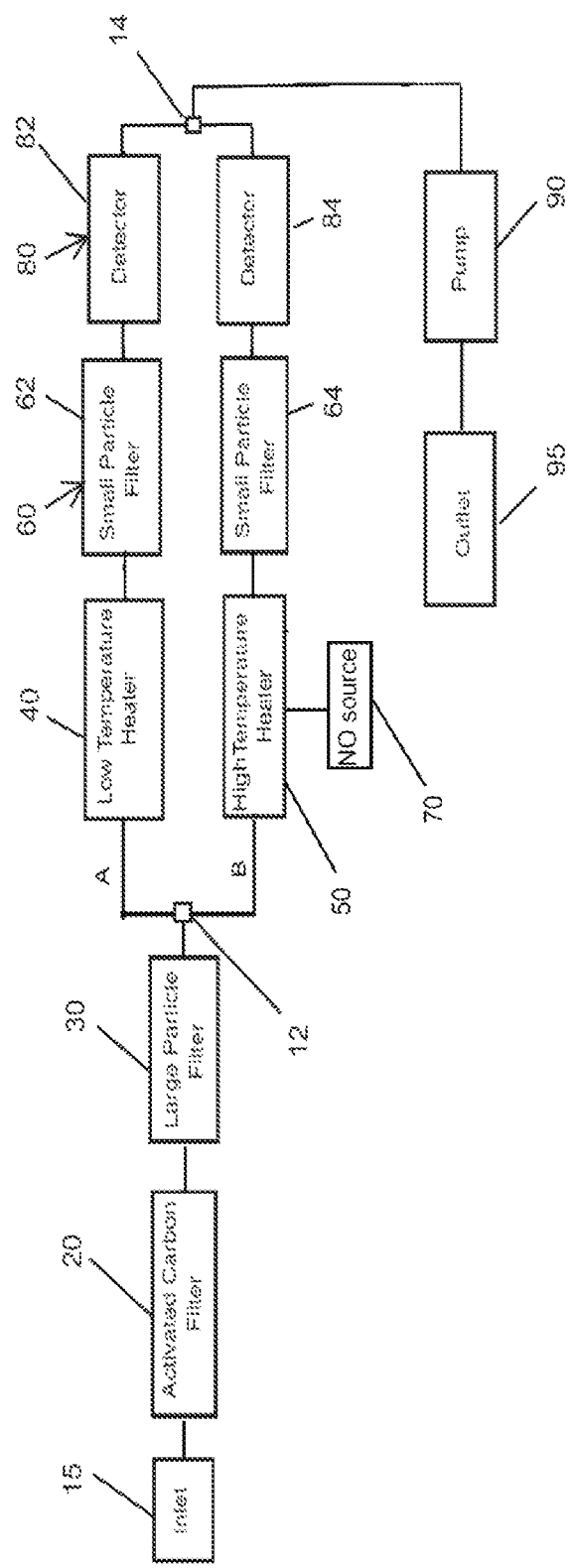
FIG. 4 is diagram of the components of an alternative embodiment of the present explosive detector.

FIG. 4 illustrates an embodiment of the present device 1 adapted to detect organic (oxygen-containing) non-nitrogenous explosive compounds. The device 1 is essentially the same as that shown in FIG. 1, except that a source of NO 70 is in communication with the high temperature heater 50. NO is introduced into the heater 50 from the source of NO 70. The heated air sample is maintained in contact with NO for a sufficient amount of time to allow nitrogen monoxide (NO) to be converted to nitrogen dioxide ($NO_2$) before the sample is introduced into the CRDS cavity or other spectrometer 82 for detection of the resultant $NO_2$.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. For example, a single channel analyzer with the higher temperature converter may be sufficient in some embodiments to avoid interferences.

Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

What is claimed is:

1. A method for detecting explosive compounds, comprising:
   (a) collecting an air sample in a vicinity of an object;
   (b) conducting the air sample through a filter comprising a porous material treated with a solution having a basic pH;
   (c) dividing the air sample into a first portion and a second portion, wherein:
      (i) the first portion of the air sample is conducted through a heater comprising a chamber heated to a temperature of between 80° C. and 200° C., in order to convert non-explosive nitrogenous compounds to NO or $NO_2$; and
      (ii) the second portion of the air sample is conducted through a heater comprising a chamber heated to a temperature of between 250° C. and 350° C., in order to convert non-explosive and explosive nitrogenous compounds to NO or $NO_2$;
   (d) spectrographically measuring the amount of $NO_2$ in both the first portion of the air sample and the second portion of the air sample; and
   (e) determining whether the amount of $NO_2$ in the second portion of the air sample is greater than the amount of $NO_2$ in the first portion of the air sample, thereby determining whether an explosive compound is present in the air sample.

2. The method of claim 1, wherein the first portion of the air sample is heated to 120° C.

3. The method of claim 1, wherein the second portion of the air sample is heated to 290° C.

4. The method of claim 1, wherein the air sample portions are conducted through the heaters for between 0.05 and 0.5 seconds.

5. The method of claim 1, wherein the porous material has been treated with a solution having a pH of between 9 and 12.

6. The method of claim 5, wherein the porous material is granular activated carbon.

7. The method of claim 5, wherein the solution comprises calcium hydroxide or magnesium hydroxide.

8. The method of claim 1, further comprising the step of passing the air sample through a filter having a pore size of between 3 and 20 microns before heating the air sample.

9. The method of claim 1, wherein the spectrographic measurement is obtained using a spectrometer selected from the group consisting of a cavity attenuated ring down spectrometer with gated integrated detection (CARDS-GID), a cavity phase shift spectroscopy (CAPS)-based instrument, a cavity enhanced absorption analyzer (CEAS), and a laser-induced fluorescence detector (LIF).

10. A device for detecting explosive compounds in an air sample, comprising:
   (a) an inlet for receiving the air sample;
   (b) a filter downstream of the inlet, the filter comprising a porous material treated with a solution having a basic pH;
   (c) a first conduit for receiving a first portion of the air sample, the first conduit being in communication with:
      (i) a first heater adapted to heat the sample to a temperature of between 80° C. and 200° C.; and
      (ii) a first spectrometer for measuring a quantity of $NO_2$ in the first portion of the air sample;
   (d) a second conduit for receiving a second portion of the air sample, the second conduit being in communication with:
      (i) a second heater adapted to heat the sample to a temperature of between 250° C. and 350° C.; and
      (ii) a second spectrometer for measuring a quantity of $NO_2$ in the first portion of the air sample; and
   (e) one or more pumps in communication with the air sample for drawing the air sample into the inlet of the device and expelling the measured air sample out of an outlet of the device.

11. The device of claim 10, wherein the spectrometers are selected from the group consisting of a cavity attenuated ring down spectrometer with gated integrated detection (CARDS-GID), a cavity phase shift spectroscopy (CAPS)-based instrument, cavity enhanced absorption (CEAS), and a laser-induced fluorescence detector (LIF).

12. The device of claim 10, further comprising a sampling tube within the inlet of the device, wherein the sampling tube directs the first portion of the air sample and the second portion of the air sample to the filter comprising activated carbon.

13. The device of claim 10, further comprising a source of nitrogen monoxide in communication with the second heater.

14. The device of claim 10, wherein the porous material has been treated with a solution having a pH of between 9 and 12.

15. The device of claim 14, wherein the porous material is granular activated carbon.

16. The device of claim 14, wherein the solution comprises calcium hydroxide or magnesium hydroxide.

17. A method for detecting explosive compounds, comprising:
   (a) collecting an air sample in a vicinity of an object;
   (b) conducting the air sample through a filter comprising granular activated carbon treated with a solution having a pH of between 9 and 12;
   (c) conducting the air sample through a heater comprising a chamber heated to a temperature of between 250° C. and 350° C., in order to convert non-explosive and explosive nitrogenous compounds to $NO_2$;
   (d) spectrographically measuring the amount of $NO_2$ in the air sample; and
   (e) determining the amount of $NO_2$ in the air sample, thereby determining whether an explosive compound is present in the air sample.

18. The method of claim 17, wherein the air sample is conducted through the heater for between 0.05 and 0.5 seconds.

19. The method of claim 17, wherein the solution comprises calcium hydroxide or magnesium hydroxide and has a pH of 10.

* * * * *